(12) United States Patent
Noori et al.

(10) Patent No.: US 8,173,415 B2
(45) Date of Patent: May 8, 2012

(54) SINGLE CELL MICROINJECTION USING FLEXIBLE AND COMPLIANT FLUIDIC CHANNELS AND ELECTROOSMOTIC DOSAGE CONTROL

(75) Inventors: Arash Noori, Whitby (CA); Ponnambalam R. Selvaganapathy, Hamilton, CA (US)

(73) Assignee: McMaster University, Hamilton (CA)

( * ) Notice: Subject to any disclaimer, the term of this patent is extended or adjusted under 35 U.S.C. 154(b) by 285 days.

(21) Appl. No.: 12/576,766

(22) Filed: Oct. 9, 2009

(65) Prior Publication Data

US 2010/0093065 A1 Apr. 15, 2010

Related U.S. Application Data

(60) Provisional application No. 61/104,372, filed on Oct. 10, 2008, provisional application No. 61/225,744, filed on Jul. 15, 2009.

(51) Int. Cl.
*C12M 1/00* (2006.01)
*C12M 3/00* (2006.01)

(52) U.S. Cl. .......... 435/285.1; 435/283.1; 435/285.2

(58) Field of Classification Search ............. 204/403.1, 204/403.01
See application file for complete search history.

(56) References Cited

U.S. PATENT DOCUMENTS

| | | | | |
|---|---|---|---|---|
| 6,645,757 | B1 * | 11/2003 | Okandan et al. | 435/285.1 |
| 6,846,668 | B1 * | 1/2005 | Garman et al. | 435/285.1 |
| 2005/0250197 | A1 * | 11/2005 | Ando et al. | 435/285.1 |

OTHER PUBLICATIONS

Matsuoka et al., "High throughput easy microinjection with a single-cell manipulation supporting robot", Journal of Biotechnology, 116 (2005), pp. 185-194.
Sun et al., "Autonomous Zebrafish Embryo Injection Using a Microrobotic System", Proceedings of the 3rd Annual IEEE Conference on Automation Science and Engineering (2007), pp. 363-368.
Chun et al., "Fabrication of Array of Hollow Microcapillaries Used for Injection of Genetic Materials into Animal/Plant Cells", Japanese Journal of Applied Physics, 38 (1999), pp. 279-281.
Lee et al., "Microfluidic valve with cored glass microneedle for microinjection", Lab Chip, 3 (2003), pp. 164-167.
Hsu et al., "Microcanals for micropipette access to single cells in microfluidic environments", Miniaturisation for Chemistry, Biology and Bioengineering, 4 (2004), pp. 420-424.

(Continued)

*Primary Examiner* — Michael Marcheschi
*Assistant Examiner* — Shanta G Doe
(74) *Attorney, Agent, or Firm* — Bereskin & Parr LLP/S.E.N.C.R.L., s.r.l.

(57) ABSTRACT

A microinjection device for injecting a target cell with a reagent. The microinjection device includes a flexible substrate; a target supply channel formed in the flexible substrate for receiving the target cell; a reagent supply channel formed in the flexible substrate for receiving the reagent; a suction capillary mounted within a suction channel formed in the flexible substrate, the suction capillary providing suction to the target supply channel for immobilizing the target cell within the target supply channel; an injection needle mounted within a needle channel formed in the flexible substrate, the injection needle being movable between injected and un-injected positions by deforming at least a part of the flexible substrate; and a plurality of electrodes embedded in the flexible substrate, the plurality of electrodes creating a voltage potential across the injection needle to move the reagent into the target when the injection needle is in the injected position.

11 Claims, 17 Drawing Sheets

OTHER PUBLICATIONS

Andersson et al., "Microtechnologies and nanotechnologies for single-cell analysis", Current Opinion in Biotechnology, 15, 2004, pp. 44-49, Elsevier.

McDonald et al., "Poly(dimethylsiloxane) as a Material for Fabricating Microfluidic Devices", Accounts of Chemical Research, 35 (2002), pp. 491-499.

* cited by examiner

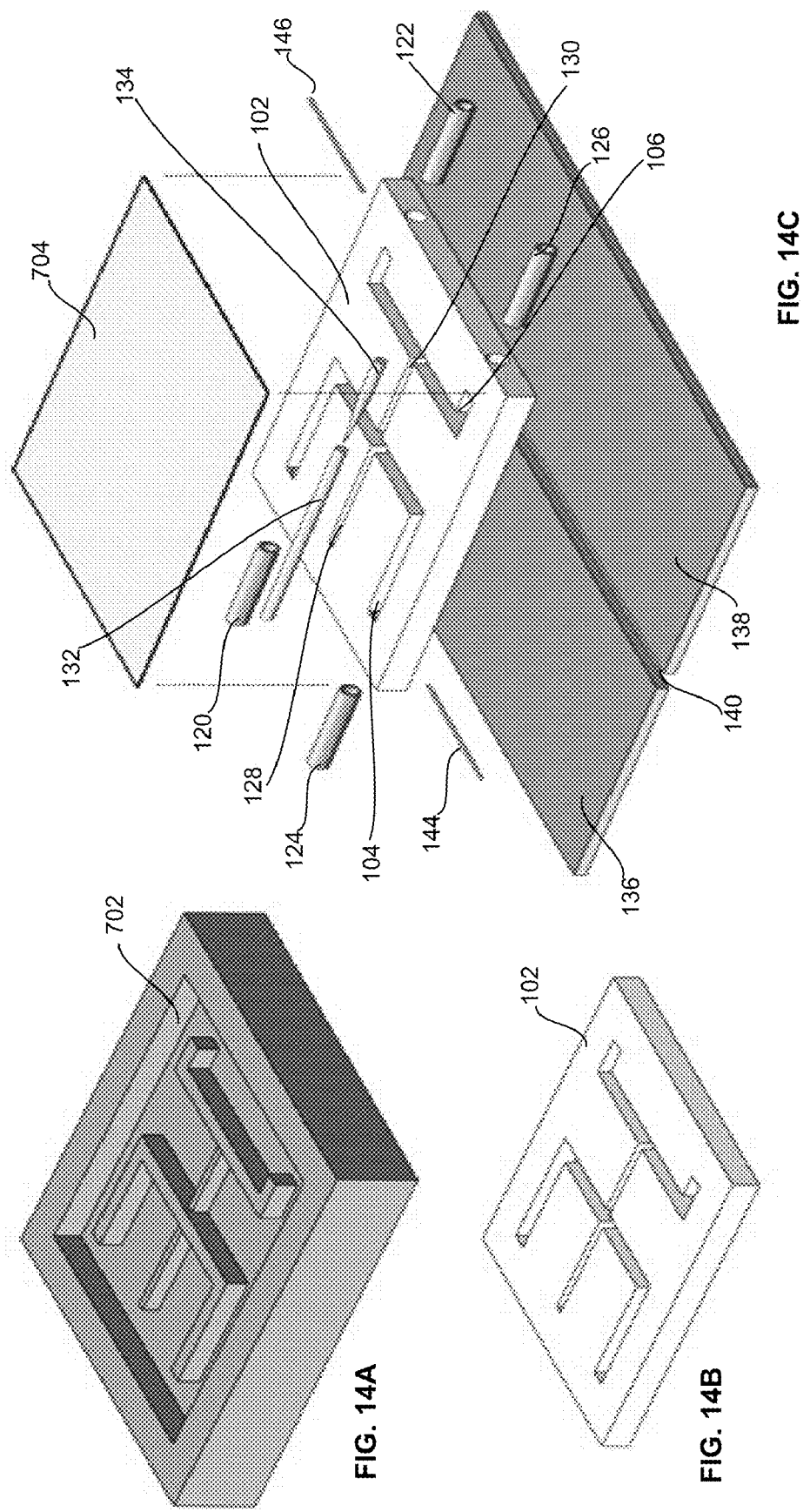

FIG. 16A  FIG. 16B
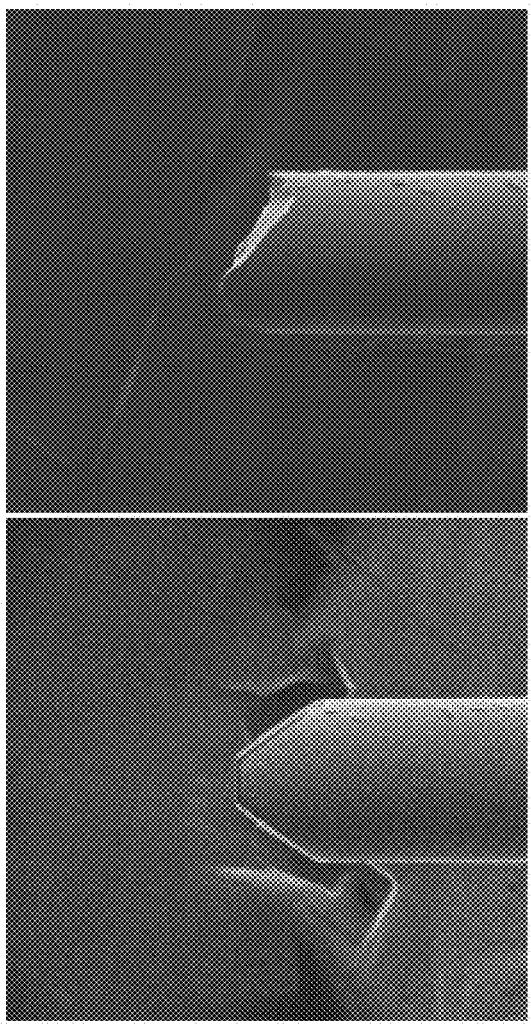
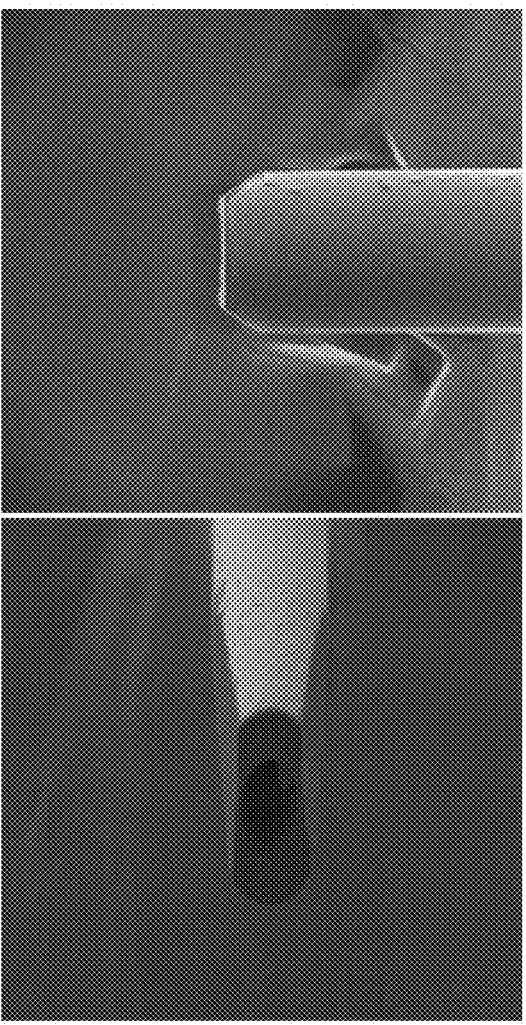
FIG. 16C  FIG. 16D

FIG. 17A
FIG. 17B
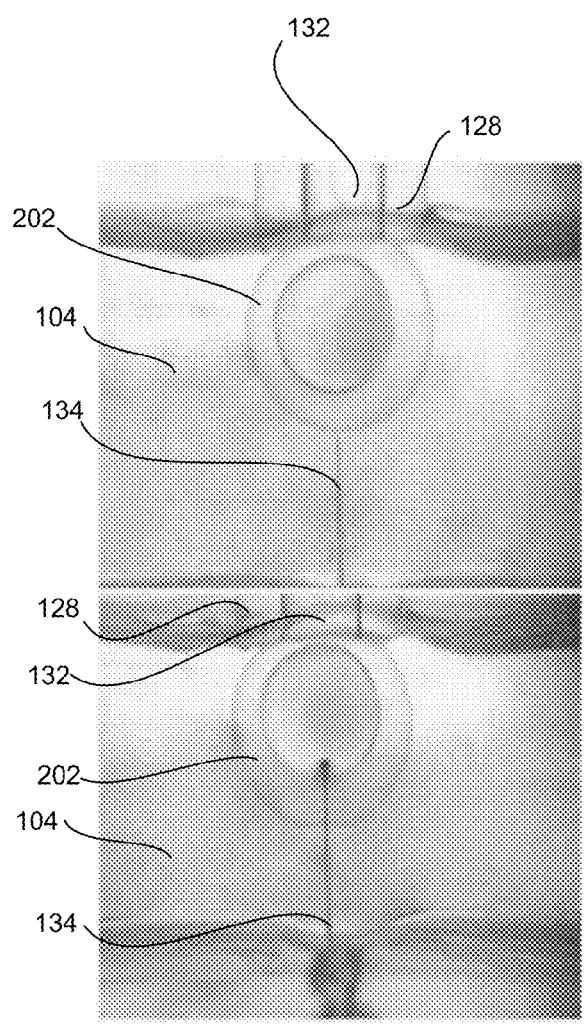
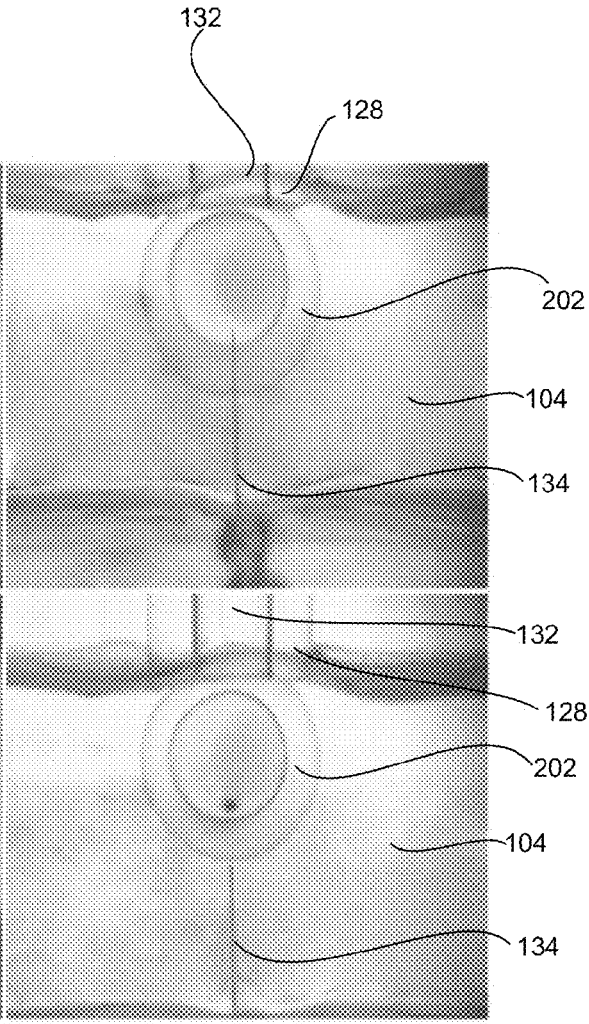
FIG. 17C
FIG. 17D

SINGLE CELL MICROINJECTION USING FLEXIBLE AND COMPLIANT FLUIDIC CHANNELS AND ELECTROOSMOTIC DOSAGE CONTROL

FIELD

The invention relates to cell injection devices and, more particularly, to a microfluidic device for high throughput injection of macromolecules, biomaterials and fluids into cells, embryos and small animals.

BACKGROUND

The introduction of protein and DNA into cells, embryos, small animals and eggs plays an important role in the fields of drug development, genetic engineering and in-vitro fertilization. It has been applied to create transgenic mammals, improve drought tolerance in plants, and to reprogram skin cells into induced pluripotent stem cells (iPS) for patent-specific stem cells. However, the efficient transfection of materials still poses a problem, and a variety of techniques, broadly classified as biological, chemical and mechanical are actively being developed.

Biological techniques employ genetically modified viruses (viral vectors) to introduce DNA into cells. This method is highly efficient, as many viruses have evolved complex mechanisms to overcome cellular barriers, but suffers from high cytotoxicity, restricted targeting of specific cell types, limited carrying capacity, production problems and high costs. Furthermore, there are concerns associated with the use of viral vectors for applications in humans, such as neutralisation by serum anti-bodies and immunogenic reactions.

This has led to the development of synthetic chemical vectors such as lipoplexes (liposome complexes) to allow delivery of material into cells. Prior to delivery, negatively charged DNA molecules are complexed with uptake enhancing transfection reagents. These complexes then bind to cells and are internalized, typically by endocytosis. Although this approach is relatively simple and safe, efficiency remains poor due to low uptake across the plasma membrane, inadequate release of DNA molecules and lack of nuclear targeting. A major barrier to efficiency is the degradation caused by enzymes within endosomes and lysosomes.

Physical methods such as the gene gun, electroporation and sonoporation overcome some of these issues by forming transient openings in the cell membrane to introduce molecules into the cytoplasm thus avoiding endosomal and possibly lysomal degradation. This is achieved either by particle bombardment or by applying electric fields or ultrasound to induce changes in membrane permeability. Although these methods increase transfection efficiency, this increase is directly related to increased cytotoxicity. Furthermore, they only provide limited, non-quantitative reagent transfection. In addition, degradation by enzymes within the cytoplasm remains a problem.

One physical method that overcomes the aforementioned problems is capillary microinjection. Transfection is achieved through the direct insertion of a microinjection needle into the cell using a microscope and precision micromanipulators. Two capillary microinjection techniques exist, differing in the mechanism used for reagent transport. These are capillary pressure microinjection (CPM), which uses pressure driven flow (PDF), and ionophoresis, which employs electrokinetic principles (electrophoresis) for reagent transport.

Of these two methods, CPM is most widely used as it is the simplest and most direct way to inject extracellular material in a targeted fashion (cytoplasm or nucleus) without cell or reagent restrictions. A wide range of substances, including naked DNA, RNA, antibodies and nanoparticles have been injected into cells with high transfection efficiency (up to 100%) and low cytotoxicity. However, the use of PDF for reagent delivery limits the efficacy of CPM. It has been shown that the volume delivered into cells may vary by a factor of five or more, resulting in significant variability and low reproducibility of injections. The use of PDF also imposes limits on the minimum injection needle size because of the high pressures that are required for dosing. Existing commercial injection systems or devices operate in the order of the 500 kPa which restricts the minimum tip diameter to 0.2-0.5 µm. This limitation on the tip diameter is significant as smaller tips lead to increased viability as they reduce the damage inflicted into cells during injection.

To enable the use of smaller needles, non-pressure driven reagent delivery such as ionophoresis may be employed. Ionophoresis involves the insertion of electrodes into the injection needle and into the cell medium to generate an electric field that induces electrophoresis. Ionophoresis overcomes the limitations on tip size as it is independent of needle geometry. However, reagent delivery is slow and is dependent on the properties of the ions to be injected. Furthermore, quantization of the reagent delivered remains a challenge. These factors make ionophoretic reagent delivery impractical for clinical studies.

In addition to the limitations associated with the reagent delivery, capillary microinjection suffers from low throughput and variability as it is an operator-mediated process. It requires a trained operator to perform the injections, which allows only for a few hundred transfections per experiment. This makes capillary microinjection impractical for studies that require statistically significant sample sizes. Furthermore, the success rate of injections is largely dependent on the operator's ability to orient the needle and holding pipette in a three-dimensional space. This results in variability and low reproducibility due to human error.

To address these issues, a number of semi and fully automated microrobotic injection systems and devices have been developed to enable rapid injection of Drosphila and Zebrafish embryos. However, these standalone systems are costly and lack integratability which makes them unsuitable for studies that require large sample sizes, as in the field of drug discovery.

This problem of integration and throughput can be addressed by the application of microfluidic technology. Performing cell injections in a microfluidic format allows for integration of pre and post-processing operations such as cell culture, sorting, and viability testing. Integration also reduces potential damage to the cell caused by changes in the cell environment. Other advantages of microfluidics include greater selectivity, reduced dead volume and automation.

Microfluidic technologies have been applied in a number of devices for microinjection of cells. Of these devices, only one approaches high-throughput injections. The device features a stationary injection needle where cells are impinged on by hydrodynamic pressure. However, the functionality of the device is limited and it is not truly scalable. As the needle is stationary in the device, it is does not compensate for differences in cell sizes and also loses location selectivity for the injection. Furthermore, the device uses pressure driven flow for injections and therefore also suffers from dosing and needle size restriction.

SUMMARY

In one broad aspect, there is provided a microinjection device for injecting a target cell with a reagent. The microinjection device includes a flexible substrate; a target supply channel formed in the flexible substrate for receiving the target cell; a reagent supply channel formed in the flexible substrate for receiving the reagent; a suction capillary mounted within a suction channel formed in the flexible substrate, the suction capillary providing suction to the target supply channel for immobilizing the target cell within the target supply channel; an injection needle mounted within a needle channel formed in the flexible substrate, the injection needle being movable between an injected position and an un-injected position by deforming at least a part of the flexible substrate; and a plurality of electrodes embedded in the flexible substrate, the plurality of electrodes creating a voltage potential across the injection needle to move the reagent into the target when the injection needle is in the injected position.

In a feature of that aspect, the target supply channel, the reagent supply channel, the suction capillary, the injection needle and the plurality of electrodes lie in a single plane of visualization.

In another feature of that aspect the microinjection devices also includes first and second rigid substrates, the flexible substrate being mounted to the first and second rigid substrates so that the flexible substrate is deformable by moving the second rigid substrate in at least one direction with respect to the first rigid substrate. In another feature of that aspect, the microinjection devices also includes a micropositioner for moving the second rigid substrate in the at least one direction. The micropositioner may be manual or automated.

In another feature of that aspect, the second rigid substrate is movable in a single linear direction. In another feature of that aspect, the suction channel and the needle channel are situated on an axis perpendicular to the target supply channel, and the second rigid substrate is linearly moveable along the axis.

In another feature of that aspect, the reagent is moved into the injection needle by electroosmotic flow induced by the voltage potential. The reagent may also be moved into the injection needle by electrophoretic flow.

In another feature of that aspect, the location of the injection needle is determined based on electrical current generated by the electrical potential. The location of the injection needle may also be determined by the resistance in the conduction path.

Further aspects and advantages of the embodiments described herein will appear from the following description taken together with the accompanying drawings.

BRIEF DESCRIPTION OF THE DRAWINGS

For a better understanding of embodiments of the devices and methods described herein, and to show more clearly how they may be carried into effect, reference will be made, by way of example, to the accompanying drawings in which:

FIG. 14A is a perspective view of a base mold used to generate the flexible substrate of FIG. 1 in accordance with an embodiment;

FIG. 14B is a perspective view of a flexible substrate generated from the base mold of FIG. 14A in accordance with an embodiment;

FIG. 14C is a perspective view of the assembly of the microinjection device of FIG. 1 in accordance with an embodiment;

FIGS. 16A to 16C are side views of an injection needle being cleaved using a Focused-Ion-Beam system in accordance with an embodiment;

FIG. 16D is a front view of an injection needle that has been cleaved using a Focused-Ion-Beam system in accordance with an embodiment; and FIGS. 17A to 17D are top views of a Zebrafish embryo being injected with methylene blue using the microinjection device of FIG. 1 in accordance with an embodiment.

Figure 1:
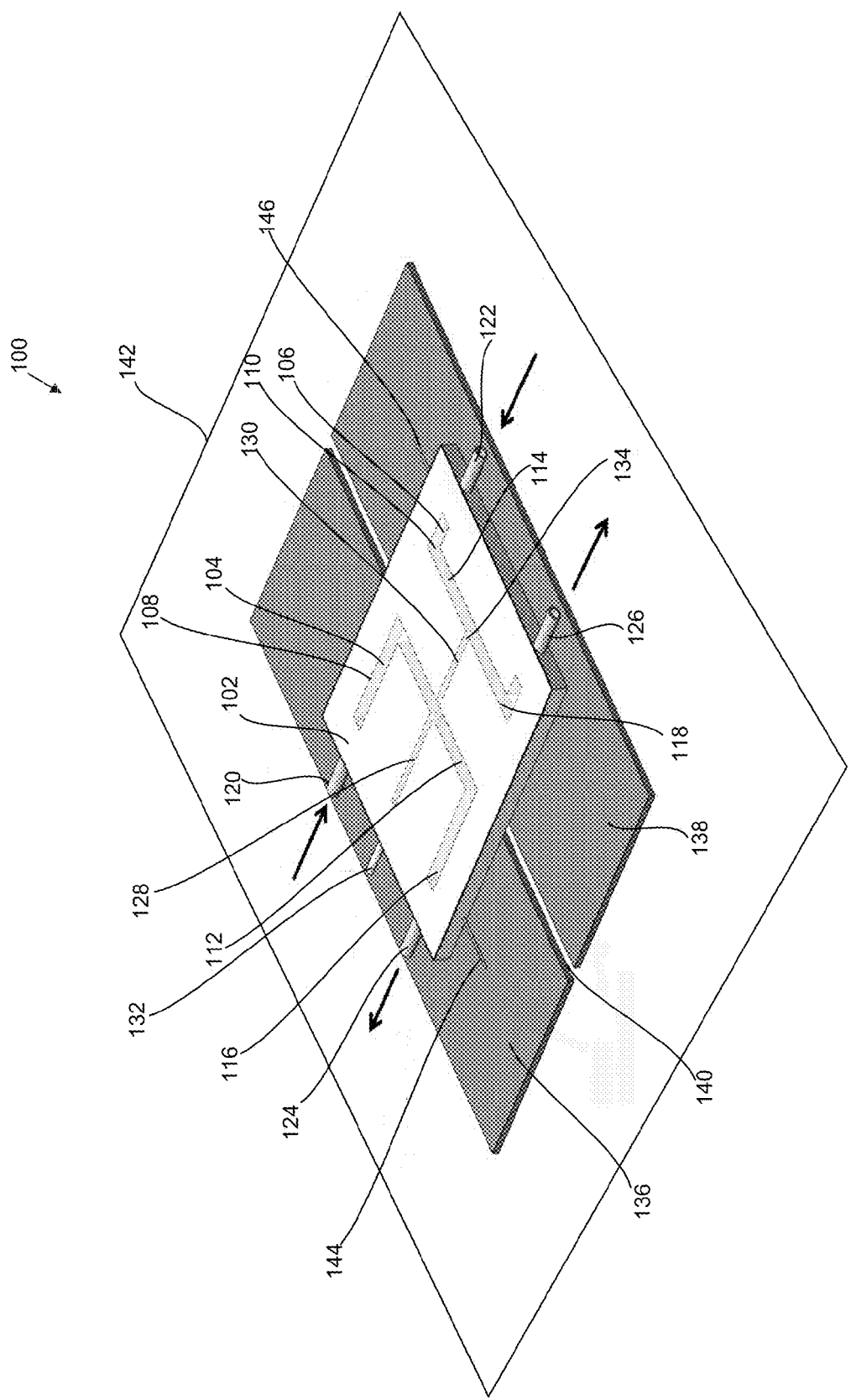
FIG. 1 is a top view of a microinjection device in accordance with an embodiment.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

Embodiments described herein relate to microinjection devices for injecting targets with a reagent using electroosmosis flow (EOF). The term "target" will be used herein to mean a cell, embryo, small animal, egg or the like. In some embodiments, the injection is preformed by an integrated injection needle which is actuated by the compliant deformation of a flexible substrate, such as a polydimethylsiloxane (PDMS) substrate.

Reference is made to FIG. 1, which illustrates a microinjection device 100 in accordance with an embodiment. The microinjection device 100 includes a flexible substrate 102, such as a polydimethylsiloxane (PDMS) substrate, having a target supply channel 104 and a reagent supply channel 106 formed therein. The target supply channel 104 supplies the injection targets, and the reagent supply channel 106 supplies the reagent (for example, food dye). In one embodiment, the target and reagent supply channels 104 and 106 are 2 mm deep and 2 mm wide.

In some embodiments, each of the target and reagent supply channels 104 and 106 have three sections: an inlet section 108, 110 for receiving the targets or reagent; a main or reservoir section 112, 114 for housing the targets or reagent; and an outlet section 116, 118 for expelling the targets or reagent after injection or use. In some embodiments, the inlet, main and outlet sections 108, 110, 112, 114, 116 and 118 are arranged to form a U-shaped channel.

In some embodiments, small tubes or capillaries, referred to herein as inlet and outlet ports 120, 122, 124, 126 are connected to the inlet and outlet sections 108, 110, 116, 118 of the target and reagent supply channels 104 and 106 to aid in supplying and removing targets and reagent from the microinjection device 100. In some embodiments, the inlet and outlet ports 120, 122, 124 and 126 are glass capillaries with an outside diameter of 2 mm and an inside diameter of 1.5 mm. In other embodiments, the inlet and outlet ports 120, 122, 124 and 126 may be made of other suitable materials and have other suitable dimensions.

The microinjection device 100 also includes a suction channel 128 and a needle channel 130 formed in the flexible substrate 102. The suction and needle channels 128 and 130 are typically shallower and narrower than the target and reagent supply channels 104 and 106. For example, in one embodiment, both the suction and needle channels 128 and 130 are 1.5 mm deep and 1 mm wide.

The suction channel 128 is situated perpendicular to the target supply channel 104 so that it intersects the main section 112 of the target supply channel 104. The suction channel 128 is used to immobilize the targets in the main section 112 of the target supply channel 104 using suction. In some embodiments, a hollow tube or capillary, referred to herein as a suction capillary 132, is inserted in the suction channel 128 to aid in providing the appropriate suction. The suction capillary 132 is typically made of glass. However, the suction capillary 132 may be made of other suitable material. In some embodiments, the suction capillary 132 has a 1 mm outer diameter (OD) and a 0.5 mm inner diameter (ID). In other embodiments, the suction capillary 132 may have other suitable dimensions.

The needle channel 130 is collinear with the suction channel 128 and connects the target and reagent supply channels 104 and 106. The needle channel 130 houses an injection needle 134, such as a microinjection needle, for providing the reagent to the target. In some embodiments, the injection needle 134 has a 15 µm outer diameter (OD) and a 7.5 µm inner diameter (ID) tip. In other embodiments, the injection needle 134 has other suitable dimensions. The injection needle 134 is actuated by the compliant and preferential deformation of the flexible substrate 102. When the injection is completed the injection needle 134 is retracted, and the target is released back into the target supply channel 104.

The flexible substrate 102 is mounted on two rigid substrates 136 and 138. In some embodiments, the rigid substrates 136 and 138 are made of glass. However, in other embodiments, the rigid substrates 136 and 138 may be made of other suitable materials. The flexible substrate 102 is mounted on the two rigid substrates 136 and 138 so that (i) there is a gap 140 between the two rigid substrates 136 and 138; and (ii) the main or reservoir section 112 of the target supply channel 104 is situated in the gap 140. In this manner, the bottom wall of the main section 112 of the target supply channel 104 is not supported by either of the rigid substrates 136 and 138.

In some embodiments, the width of the gap 140 is equal to the width of the target supply channel 104. For example, if the target supply channel 104 has a width of 2 mm, the rigid substrates 136 and 138 may be placed 2 mm apart to accommodate the main section 112 of the target supply channel 104.

The two rigid substrates 136 and 138 are mounted on a fixture 142, such as a glass fixture, so that the first rigid substrate 136 is fixed and the second rigid substrate 138 is moveable with respect to the fixture 142. In one embodiment, the second rigid substrate 138 is moveable only in a single linear direction. For example, the second rigid substrate 138 may be movable in the linear direction perpendicular to the target supply channel 104. In other embodiments, the second rigid substrate 138 may be moveable in multiple directions. For example, the second rigid substrate 138 may be moveable in 3D.

The microinjection device 100 also includes two electrodes 144 and 146 embedded within the flexible substrate 102. The first electrode 144 is inserted in the target supply channel 104 and the second electrode 146 is inserted into the reagent supply channel 106. The electrodes 144 and 146 are used apply a voltage potential across the target and reagent supply channels 104 and 106 to induce electroosmotic flow (EOF) of the reagent through the injection needle 134. In some embodiments, the electrodes 144 and 146 are 30 gauge stainless steel needles. However, in other embodiments, other suitable electrodes may be used.

Generally the microinjection device 100 of FIG. 1 works as follows. First, a target is loaded into the target supply channel 104. Suction is applied to the suction capillary 132 to immobilize the target at the injection site. Once, the target is immobilized, the second rigid substrate 138 is actuated to move the injection needle 134 into the injected position. In the injected position the injection needle 134 pierces the target. Once the target has been pierced an electrical voltage is applied across the injection needle 134 using the embedded electrodes 144 and 146 to move the reagent into the injection needle 134 and ultimately into the target. After the reagent has been injected into the target, the injection needle 134 is moved away from the target and the target is released back into the target supply channel 104. The injected target then exits the device 100 via the outlet section 116 of the target supply channel 104. A detailed description of each of these steps will be described below in reference to FIGS. 2 to 12.

Figures 2A, 2B:
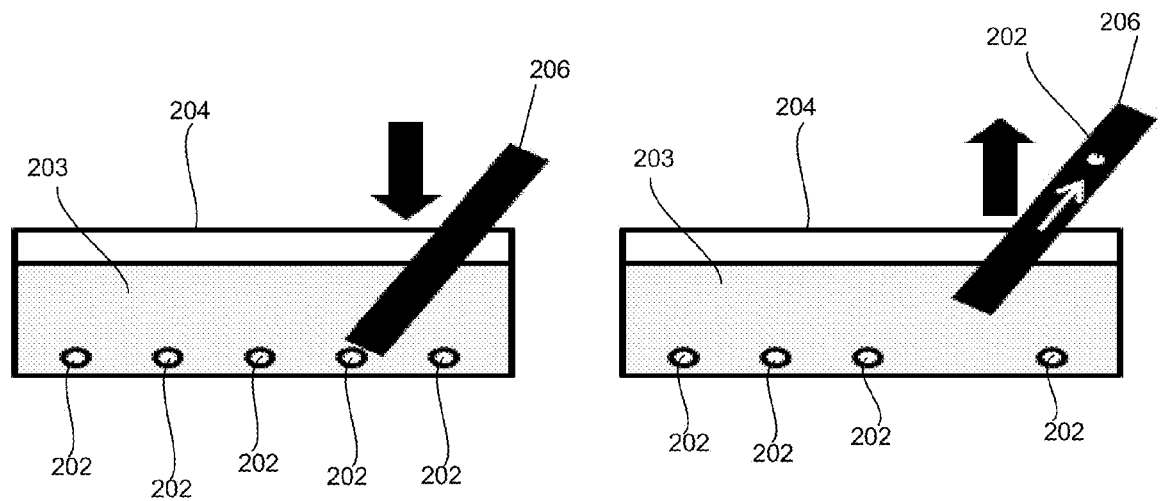
FIGS. 2A and 2B are a schematic illustrating a method for loading targets into the microinjection device of FIG. 1 in accordance with an embodiment.

Reference is now made to FIGS. 2A and 2B, in which a method of loading targets 202 into the microinjection device 100 of FIG. 1 in accordance with an embodiment is illustrated. Initially, the targets 202 are placed in a container 204, such as a Petri dish, in a buffer medium 203. The targets 202 are then loaded into the target supply channel 104 through an inlet tube 206 that is connected to the target supply channel inlet port 120. Specifically, the inlet tube 206 is brought in close proximity to a target 202 which is then loaded into the target supply channel 104 by applying suction to an outlet tube (not shown) connected to the target supply channel outlet port 124. Once a target 202 has been loaded into the inlet tube 206 the inlet tube 206 is typically moved away (i.e. raised) from the container 204 to prevent loading of other targets 202, while ensuring uninterrupted suction. One of the advantages of this method is that the target 202 remains in the original buffer medium 203 which has been shown to reduce environmental shocks that can affect viability. The loading may proceed in a continuous fashion with predetermined spacing with each target.

Figure 3:
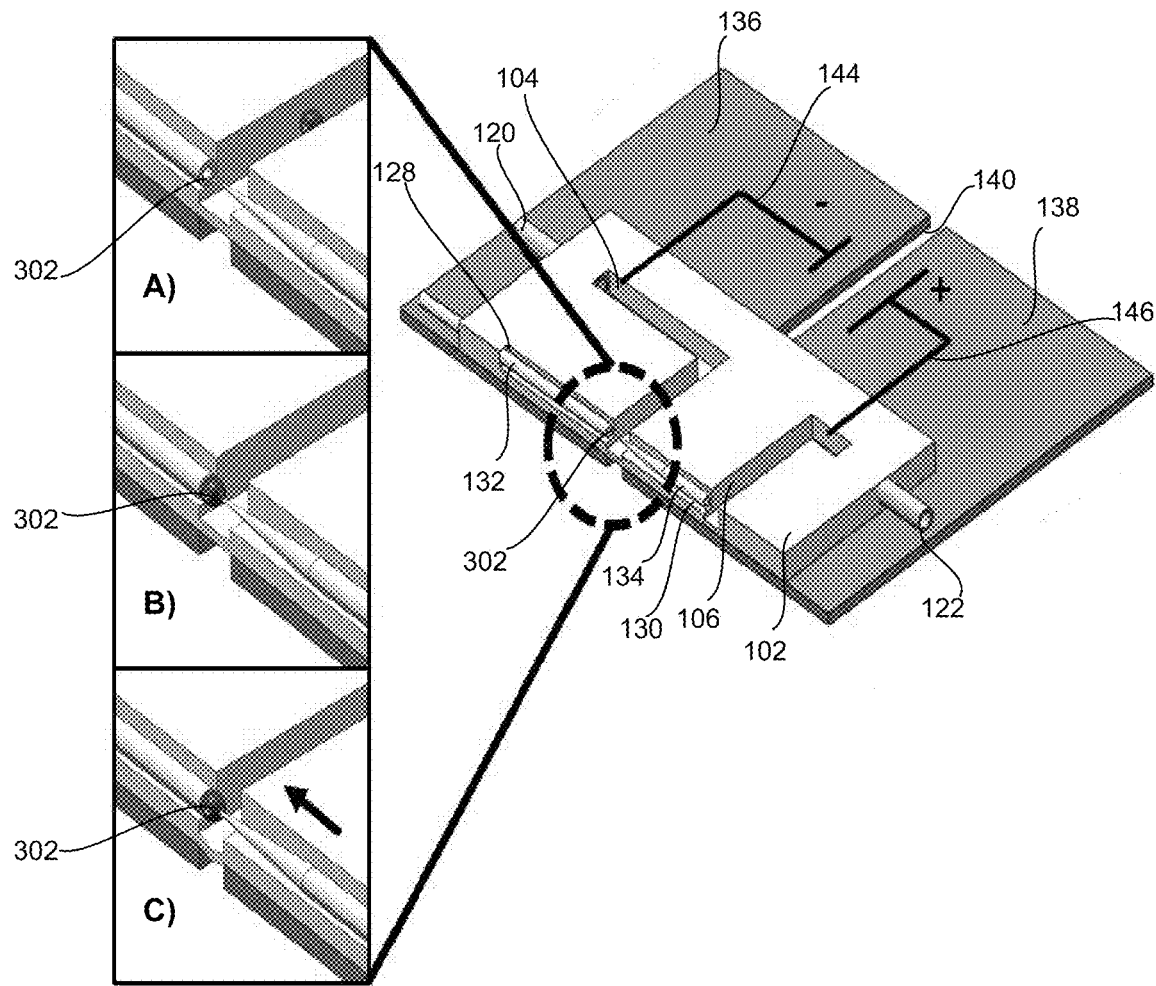
FIG. 3 is a cross section view of the microinjection device of FIG. 1 illustrating a method for injecting a target in accordance with an embodiment.

Reference is now made to FIG. 3, in which a method of injecting a target with a reagent using the microinjection device 100 of FIG. 1 in accordance with an embodiment is illustrated. When a target 202 has been loaded into the target supply channel 104 (by, for example, the method described in reference to FIGS. 2A and 2B), it is transported to the injection site 302. The target 202 is held or immobilized at the injection site 302 by applying suction to the suction capillary 132 using, for example, a syringe (not shown) attached to the suction capillary 132. Once the target 202 has been immobilized, the target 202 is injected with the reagent by actuating the injection needle 134.

In one embodiment, the injection needle 134 is actuated by the compliant deformation of the top and bottom walls of the target supply channel 104. Specifically, as described above, in reference to FIG. 1, the flexible substrate 102 is mounted on two rigid substrates 136 and 138 so that (i) there is a gap 140 between the rigid substrates 136 and 138; and (ii) the bottom wall of the main section 112 of the target supply channel 104 is situated in the gap 140. The first rigid substrate 136, is fixed, and the second rigid substrate 138 is moveable.

Figure 4:
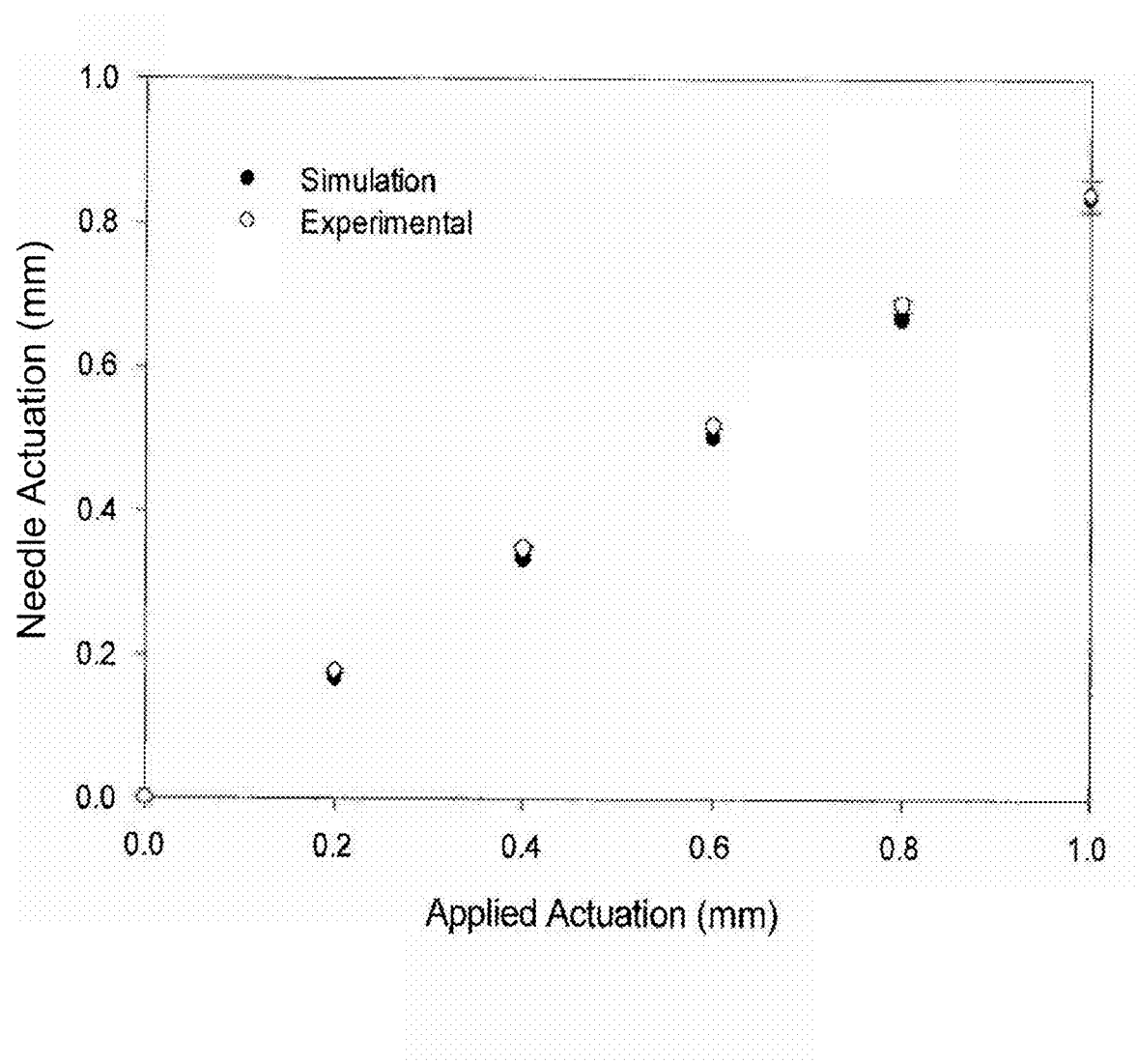
FIG. 4 is a graph illustrating the relationship between the displacement of the second rigid substrate and the displacement of the injection needle of FIG. 1 in accordance with an embodiment.

Applying a linear displacement to the second rigid substrate 138 causes displacement of the injection needle 134 and deformation of the target supply channel 104. However, the displacement applied to the second rigid substrate 138 is not typically equal to the displacement of the injection needle 134. Reference is made to FIG. 4, which is a graph illustrating the relationship between the displacement of the second rigid substrate 138 and the displacement of the injection needle 134. It can be seen from FIG. 4 that the effective injection needle 134 displacement is only 83.8% of the displacement applied to the second rigid substrate 134. This difference is caused by the fact that part of the displacement results in elastic strain in the flexible substrate 102.

Figure 5:
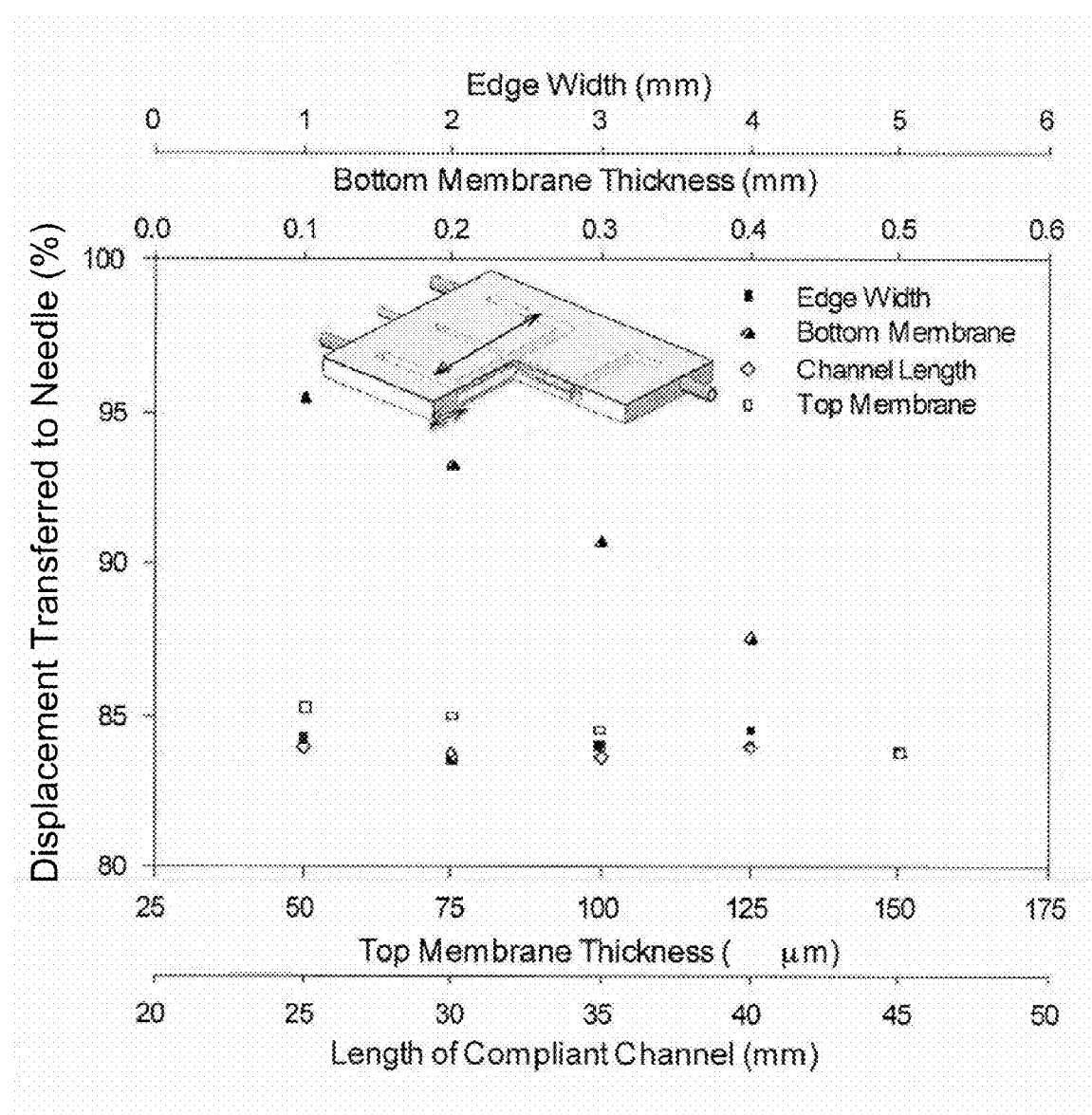
FIG. 5 is a graph illustrating the relationship between the characteristics of the flexible substrate of FIG. 1 and the effective displacement ratio for the injection needle in accordance with an embodiment.

The inventors have determined that there is a relationship between the geometry of the flexible substrate 102 (and the channels formed therein) and the effective displacement of the injection needle 134. Therefore the effective displacement of the injection needle 134 as a function of the displacement applied to the second rigid substrate 138 can be increased or decreased by adjusting the geometry of the flexible substrate 102. Reference is now made to FIG. 5, which illustrates the relationship of the following parameters to the effective displacement of the injection needle 134: the length of the main or reservoir section 112 of the target supply channel 104; the width of the membrane (the membrane is described below in reference to FIG. 13); the distance between the outlet port 124 of the target supply channel 104 and the edge of the flexible substrate 102; and the thickness of the bottom wall of the target supply channel 104.

FIG. 5 shows that adjusting the distance between the outlet port 124 of the target supply channel 104 and the edge of the flexible substrate 102 has little effect on the effective displacement of the injection needle 134. For example, reducing the distance from 5 mm to 1 mm only increased the effective displacement to 84.2%.

FIG. 5 also shows that adjusting the length of the main section 112 of the target supply channel 104 has little effect on the effective displacement of the injection needle 134. For example, reducing the length from 45 mm to 14 mm only increased the effective displacement to 83.9%.

FIG. 5 also shows that adjusting the thickness of the top membrane has little effect on the effective displacement of the injection needle 134. For example, reducing the membrane thickness from 150 μm to 50 μm only increased the effective displacement to 85.2%.

FIG. 5 does show, however, that the thickness of the bottom wall of the target supply channel 104 has a significant effect on the displacement of the injection needle 134. For example, reducing the thickness of the bottom wall of the target supply channel 104 from 0.5 mm to 0.1 mm increased the effective displacement of the injection needle 134 to 95.4%. Accordingly, care should be taken in ensuring that the thickness of the bottom wall of the target supply channel 104 is the same across microinjection devices to ensure the displacement of the injection needle 134 can be accurately predicted and controlled.

The displacement of the second rigid substrate 138 may be applied by a linear micropositioner (not shown). The micropositioner may, for example, be a single axis micropositioner or a three-axis micropositioner based on the number of direction that the second rigid substrate 138 is moveable. The micropositioner may be manual or automated.

As described above in reference to FIG. 1, the rigid substrates 136 and 138 are mounted to a fixture 142 to constrict the movement of the second rigid substrate 138 along the longitudinal direction of the injection needle 134. This ensures precise linear motion of the injection needle 134 and prevents possible damage to the targets 202 by the lateral movement of the injection needle 134.

The described injection method reduces the complexity and variability associated with microinjections. Specifically, only one degree of freedom (DOF) is used to perform the injection, which is an improvement over convention microinjection methods which involve up to five DOF for the suction capillary and the injection needle. Furthermore, as the injection occurs in a planar format it provides precise control over the microinjection location and facilitates automation.

Figure 6:
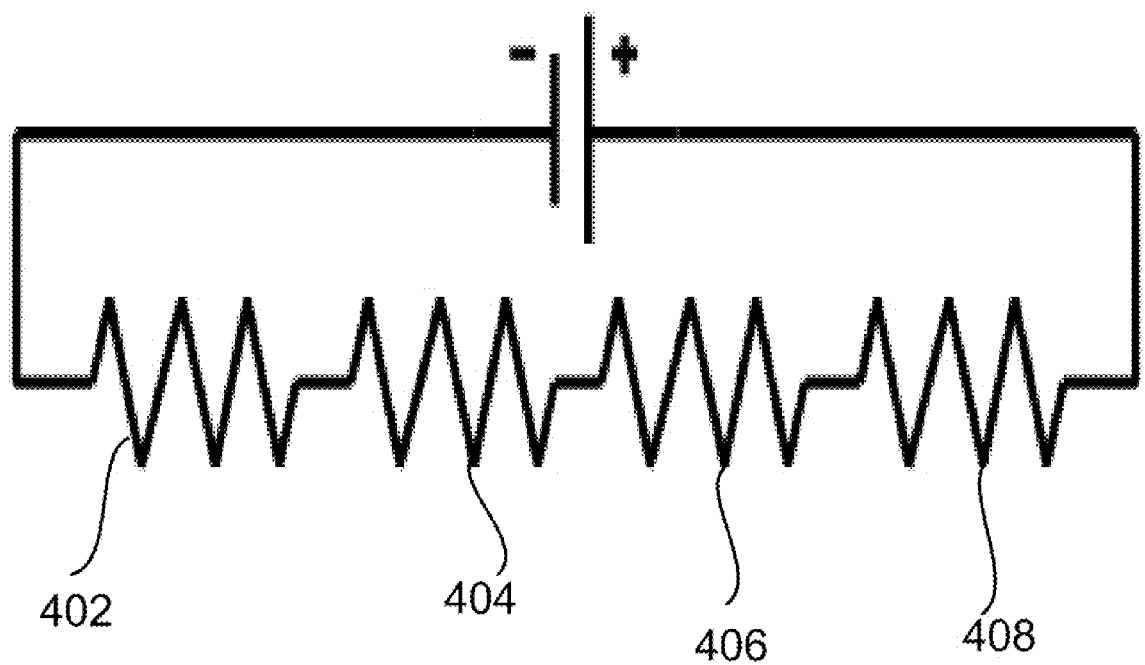
FIG. 6 is an electrical circuit diagram illustrating the conduction path when voltage is applied across the supply channels of FIG. 1 in accordance with an embodiment.

Once a target 202 has been immobilized and punctured by the injection needle 134 the reagent transport is initiated. In one embodiment, the pumping of the reagent is achieved by electroosmotic flow (EOF). EOF is described by M. J. Lukkari, M. I. Karjalainen, R. Sarkanen, M. L. Linne, T. O. Jalonen and P. J. Kallio, in 26$^{th}$ Annual International Conference of the Engineering in Medicine and Biology Society, 2004, pp. 2557-2560 herein incorporated by reference. The EOF is induced by applying a potential to the electrodes 144 and 146 embedded in the target and reagent supply channels 104 and 106 respectively. The conduction path is through the reagent solution in the reagent supply channel 106, across the injection needle 134, the target 202, and the target medium 203. Reference is made to FIG. 6, which illustrates the conduction path using electrical components. Each component in the conduction path is represented by a resistor. For example, the target supply channel 104 is represented by resistor 402, the injection needle 134 is represented by resistor 404, and the target 202 is represented by resistor 406 and the target medium 203 is represented by resistor 408.

Figure 7:
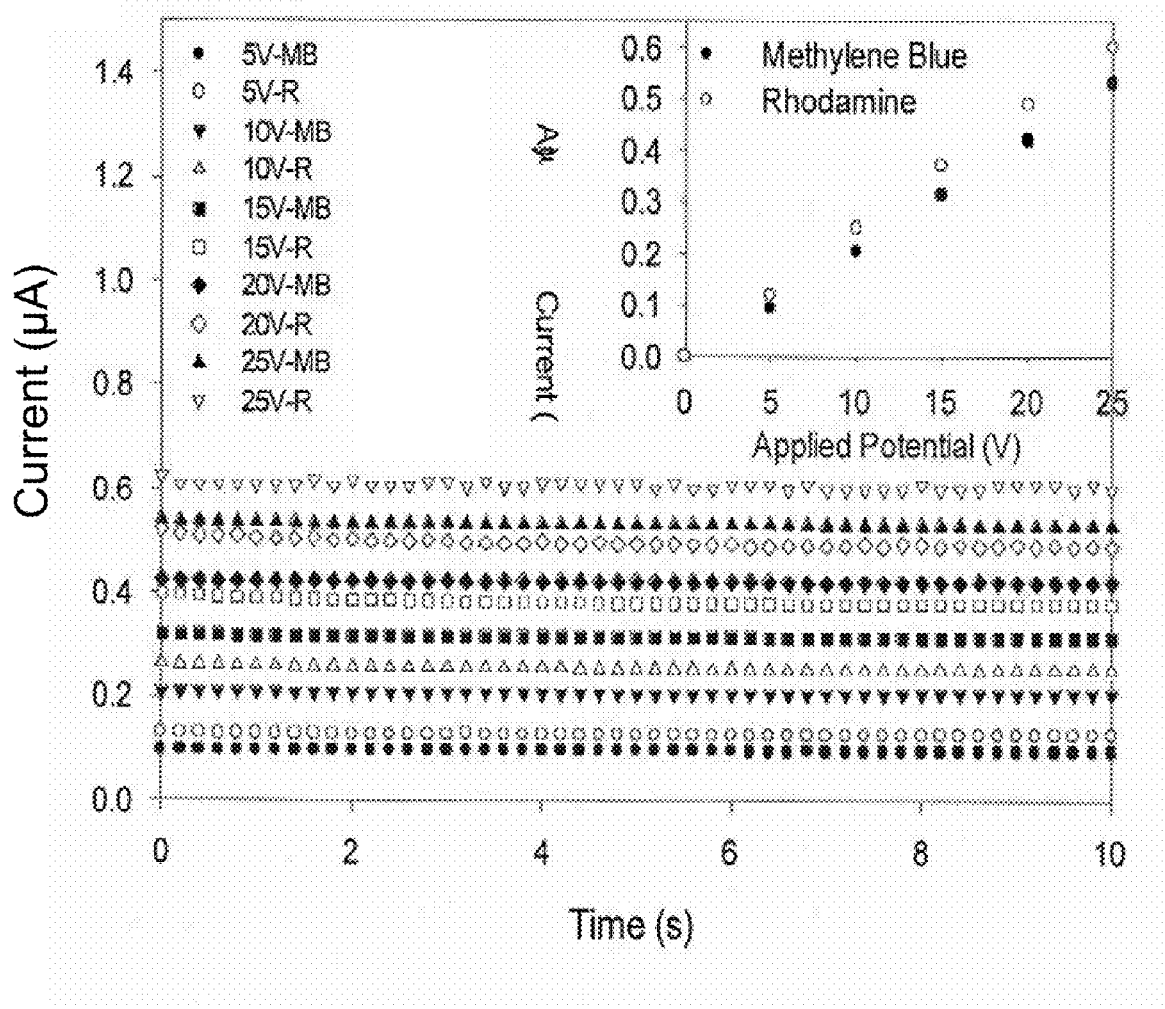
FIG. 7 is a graph illustrating the current when the microinjection device of FIG. 1 is in the un-injected state in accordance with an embodiment.
Figure 8:
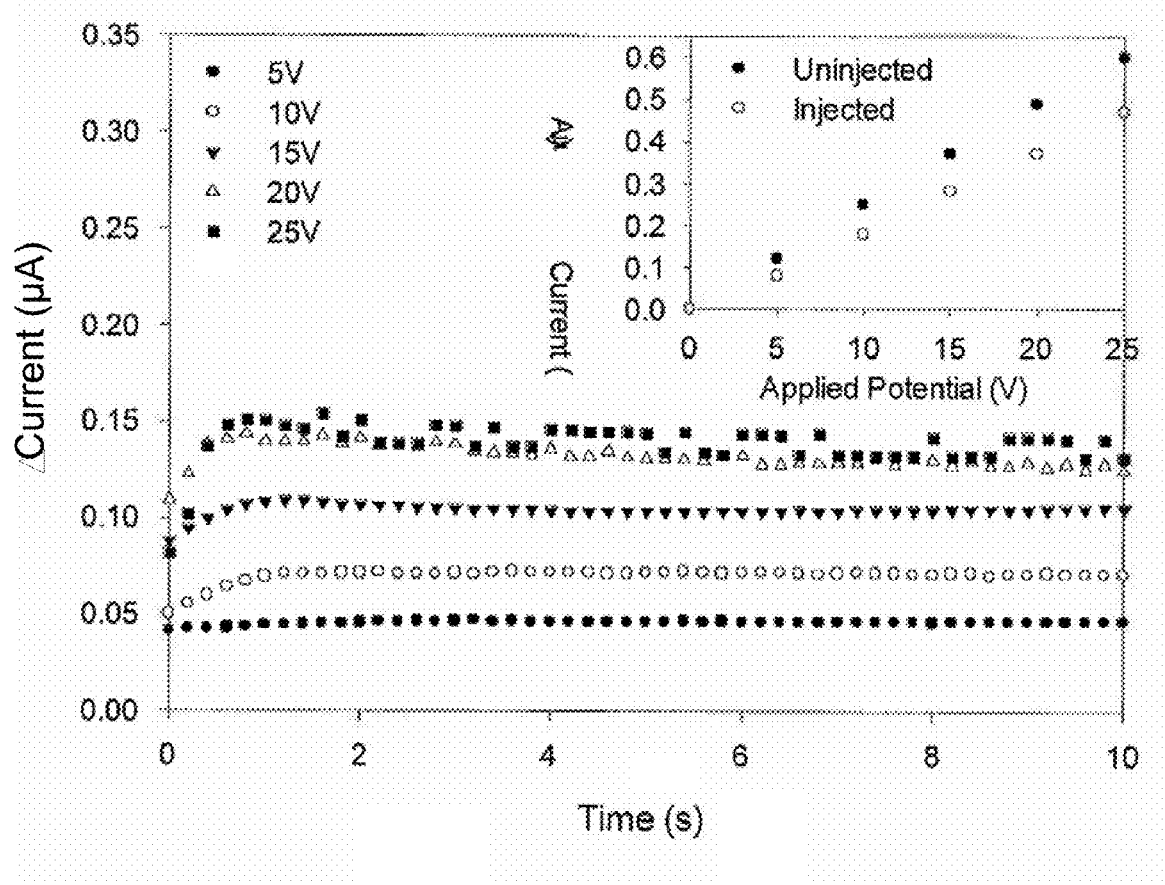
FIG. 8 is a graph illustrating the current when the microinjection device of FIG. 1 is in the injected state in accordance with an embodiment.
Figure 9:
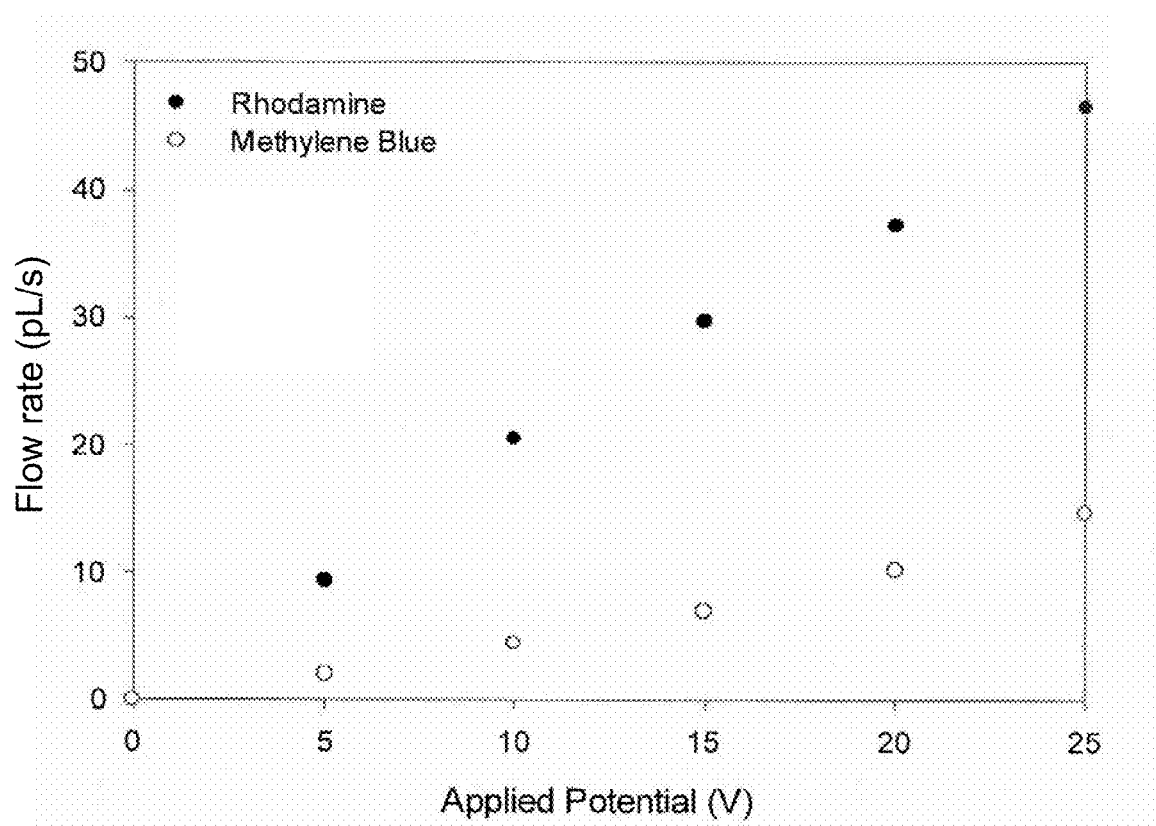
FIG. 9 is a graph illustrating the electroosmosis flow when the microinjection device of FIG. 1 is in the un-injected state in accordance with an embodiment.
Figure 10:
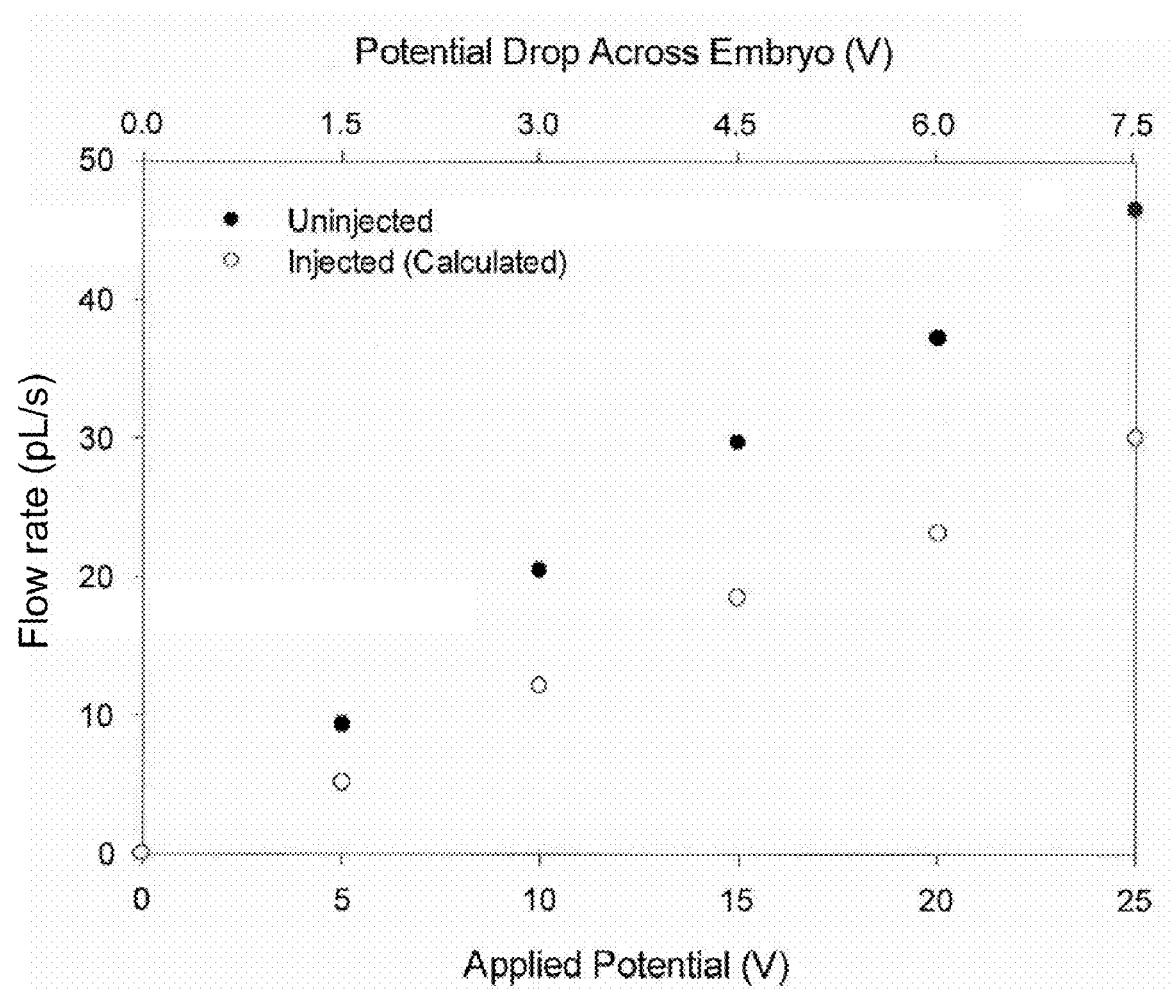
FIG. 10 is a graph illustrating the electroosmosis flow when the microinjection device of FIG. 1 is in the injected state in accordance with an embodiment.

The current flowing during EOF and the actual EOF flow rate are typically based on (i) the particular type of target; (ii) the particular type of reagent; (iii) the voltage applied; and (iv) whether the injection needle is in the un-injected or injected position. To illustrate this relationship, reference is made to FIGS. 7 to 10. Specifically, FIGS. 7 and 8 show the current flow and FIGS. 9 and 10 show the electroosmotic flow rates where the targets are Zebrafish embryos and the reagent is either rohamine B (0.005 g/mL) or methylene blue (0.04 g/mL) in a pH 10 carbonate buffer. In all cases a voltage potential range of 5V to 25V was applied.

FIG. 7 illustrates the current in the microinjection device 100 in the described conditions when the injection needle 134 is in an un-injected position. It can be seen from the values in FIG. 7 that the current for the rhodamine B solution was on average 19% greater than those obtained from the methylene blue solution. Specifically, for the voltage potential range of 5 V to 25 V, the measured currents ranged from 0.12 µA-0.60 µA for the rhodamine B, and 0.095 µA to 0.53 µA for the methylene blue solution.

FIG. 8 illustrates the delta between the current when the injection needle is in the un-injected position and the injected position. It can be seen from FIG. 8 that overall, the data exhibited consistant and predictable behavior, however, it became a bit unstable at potentials greater than 20V. Therefore, using potentials lower than 20 V may provide more accurate results in the case of a rhodamine B solution. For other solutions, the optimal range will typically vary depending on their behavior during electroosmosis.

For the rhodamine B solution, the current values that were obtained during injections ranged from 0.08 µA to 0.47 µA. These values were on average 26% lower than for the devices in the uninjected state, due to the added resistance of the embryo. The current measurements were used to deduce an added resistance of roughly 15 MΩ during injection into the embryo. The associated joule heating during injections was calculated to be between 0.4 µW and 11.8 µW. It was also found that almost 70% of the potential drop occurred across the injection needle 134. Therefore during injections the embryo was only exposed to 30% of the applied potential, which would have been 7.5 V at 25 V. Assuming that the injection occurred into the center of the embryo to a maximum electric field of 150 V/cm at 25V. This is significantly lower than the electric field strengths of up to 3,500 V/cm that are used in the electroporation of Zebrafish embryos.

FIG. 9 illustrates the measured electroosmosis flow rate when the injection needle is in an un-injected position. The electrosmosis flow rates were determined by tracking the interface between a clear pH 10 buffer solution and the methylene blue and rhodamine B solutions in the injection needle 134. Initially the injection needle 134 was completely filled with the rhodamine B or methylene blue solution by engaging the electroosmotic flow. The target channel was then flushed and care was taken to minimize pressure imbalances across the injection needle 134. Subsequently, a reverse potential was applied and the rate at which the interface between the solutions moved inside the needle was measured. The corresponding volumetric flow rate was calculated using the dimensions of the frustum through which the interface moved over a specified period.

It can be seen from FIG. 9 that the flow rates for the device in an un-injected state ranged between 9.3 pL/s to 46.5 pL/s for the rhodamine B solution and 2.1 pL/s-14.7 pL/s for the methylene blue solution.

FIG. 10 illustrates the calculated electroosmosis flow rate when the injection needle 134 is in an injected position. Due to the difficulty measuring the electroosmosis flow rate when the injection needle 134 is in the injected position, the flow rate was calculated according to the following manner. First, it was supposed that the flow rates during injection can be obtained by determining the change in the potential across the injection needle 134 caused by the presence of the embryo and then calculated using this new potential. The Smoluchowski equation shown in equation (1) was used for this purpose:

$$u_{EO} = \mu_{EO} * E \tag{1}$$

where $u_{EO}$ is the electroosmotic mobility and $\mu_{EO}$ is the electroosmotic velocity. The velocity was calculated from measured flow rates, which is a good approximation given the small taper (y/x=0.0094) in the section that was measured. $E_N$ is the electric field across the injection needle 134, which was calculated using equation (2):

$$E_N = \frac{I * R_N}{l_N} \tag{2}$$

where I is the current, $l_N$ is the total injection needle 134 length and $R_N$ is the resistance across the injection needle 134. The resistance across the injection needle 134 was calculated using equation (3):

$$R_T = R_N + R_{TC} + R_{RC} \tag{3}$$

where $R_T$ is the measured total resistance of the device, $R_{TC}$ is the resistance in the target supply channel 104, and $R_{RC}$ is the resistance in the reagent supply channel 106. By solving equations (2) and (3) and substituting, equation (1) can be solved.

The mean electroosmotic mobility for the rhodamine B flow was found to be $5.49 \times 10^{-3}$ cm$^2$/Vs. This electroosmotic mobility was then used to calculate the electroosmotic velocity and flow rate during injection into an embryo. This was done by first determining the resistance across the needle during injection, denoted $R_{N,Inj}$. The resistance was calculated using equation (4):

$$R_{T,Inj} = R_{N,Inj} + R_{TC} + R_{RC} + R_{Embryo} \tag{4}$$

where $R_{T,Inj}$ is the measured total resistance of the device and $R_{Embryo}$ is the added resistance due to the presence of the embryo. The electric field across the needle was then calculated using the resistance across the needle during injections and the measured current. This provided the effective electric field that the solution inside the injection needle 134 experiences. The new electric field was then used in combination with the electrosmotic mobility of the flow in equation (1) to obtain the flow rate during injection.

It can be seen from FIG. 10 that the calculated flow rates ranged from 5.1 pL/s to 30 pL/s which is a 40% reduction compared to the flow in the un-injected state.

One of the advantages of employing EOF for reagent transport is that it obviates the need for specialized pumps and provides true scalability to the injection needle 134. Unlike conventional pressure driven injection systems and devices, it does not place limitations on the size of the injection needle 134. Furthermore, EOF provides a non-pulsating steady plug-like flow and thus allows for precise electrical dosage control with sub-picoliter flow rates.

Figure 11:
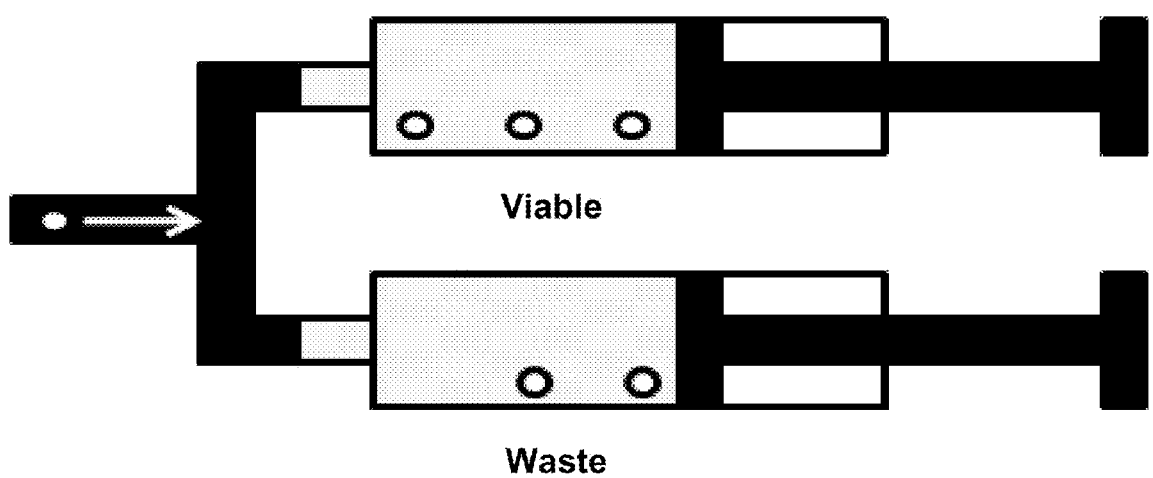
FIG. 11 is a perspective view showing a method for sorting targets using the microinjection device of FIG. 1 in accordance with an embodiment.

Reference is now made of FIG. 11 in which a method of sorting the injected targets in accordance with an embodiment is illustrated. Once the injection is completed the target 202 is transported into the appropriate viable or waste reservoir.

Another challenge in conventional capillary pressure microinjection (CPM) is the detection of damaged needles. Early detection is crucial as clogged or damaged needles may lead to variation of the reagent volume that is delivered or no delivery at all. This may lead to inconsistent results and low reproducibility for studies involving transfections. To improve reproducibility, an efficient system for detection is required to allow for remedial actions, such as the flushing or replacement of the needle, to take place.

In the microinjection device 100 of FIG. 1, the changes in the injection needle 134 can be monitored using the embedded electrodes 144 and 146. Specifically, by monitoring the current flowing through the conduction path illustrated in FIG. 6, it is possible to detect changes to the injection needle 134, as well as when the injection needle 134 makes contact with the target.

Figure 12:
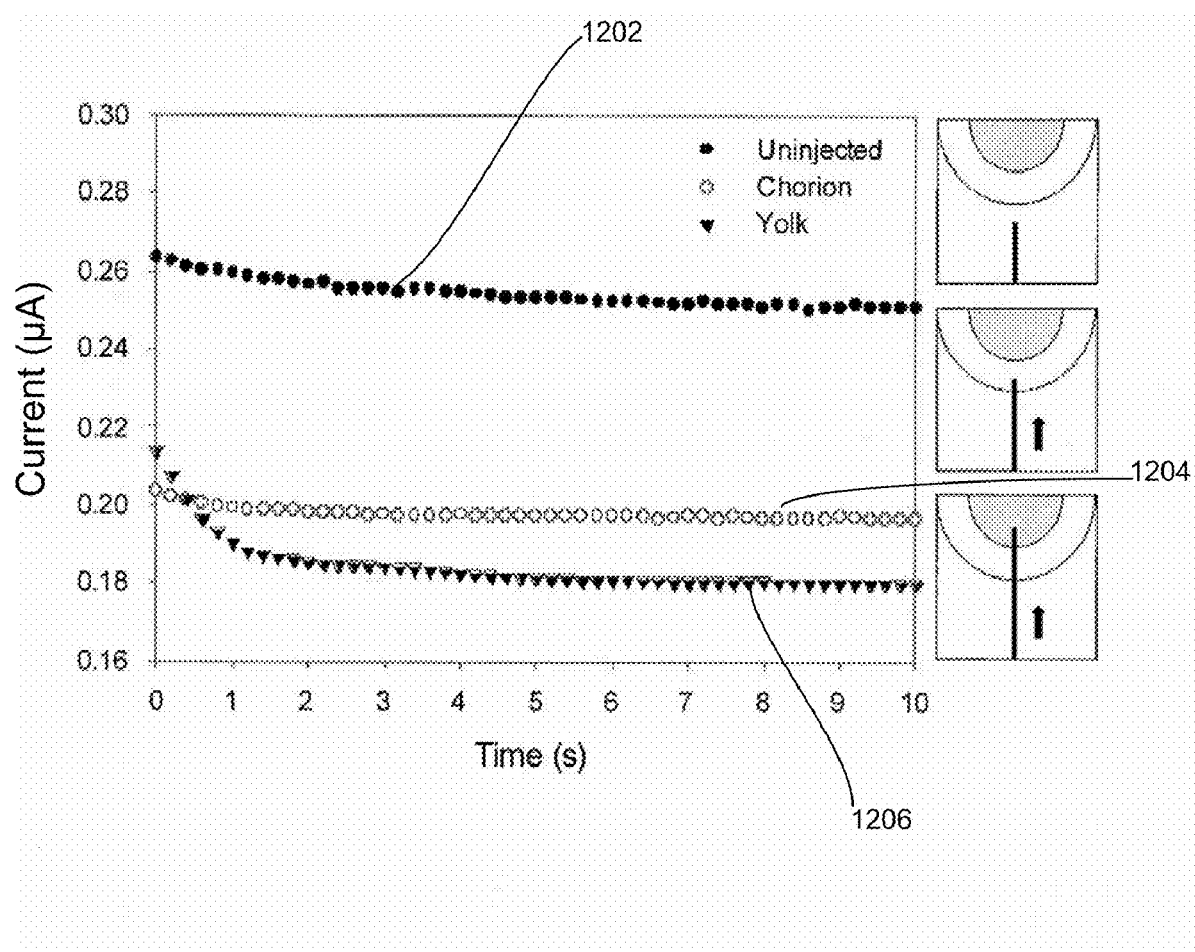
FIG. 12 is a graph illustrating the relationship between current and injection needle position in accordance with an embodiment.

Reference is now made to FIG. 12, which is a graph illustrating the relationship between current flow and injection needle 134 position. Specifically, FIG. 12 shows three curves, the first curve 1202 shows the current when the injection needle 134 is in an un-injected position, the second curve 1204 shows the current when the injection needle 134 is in a partially injected position (e.g. it has been injected into the chorion of the embryo, but not the yolk sack), and the third curve 1206 shows the current when the injection needle 134 is fully injected (e.g. it has been injected into the chorion and the yolk sack of the embryo). It can be seen from these curves that inserting the injection needle into the target/embryo reduces the current and the deeper the injection needle is injected; the more the current is reduced. For example it can be seen that inserting the injection needle 134 into the chorion caused a significant downward shift of the current from around 0.26 µA to 0.20 µA, and inserting the injection needle 134 further into the yolk sack shifted the current further down to 0.18 µA.

This relationship between current and injection needle 134 position can be used to provide real-time information about the location of the needle in the target 202. This further improves location selectivity and provides an added, non-visual feedback mechanism for automation.

Figure 13:
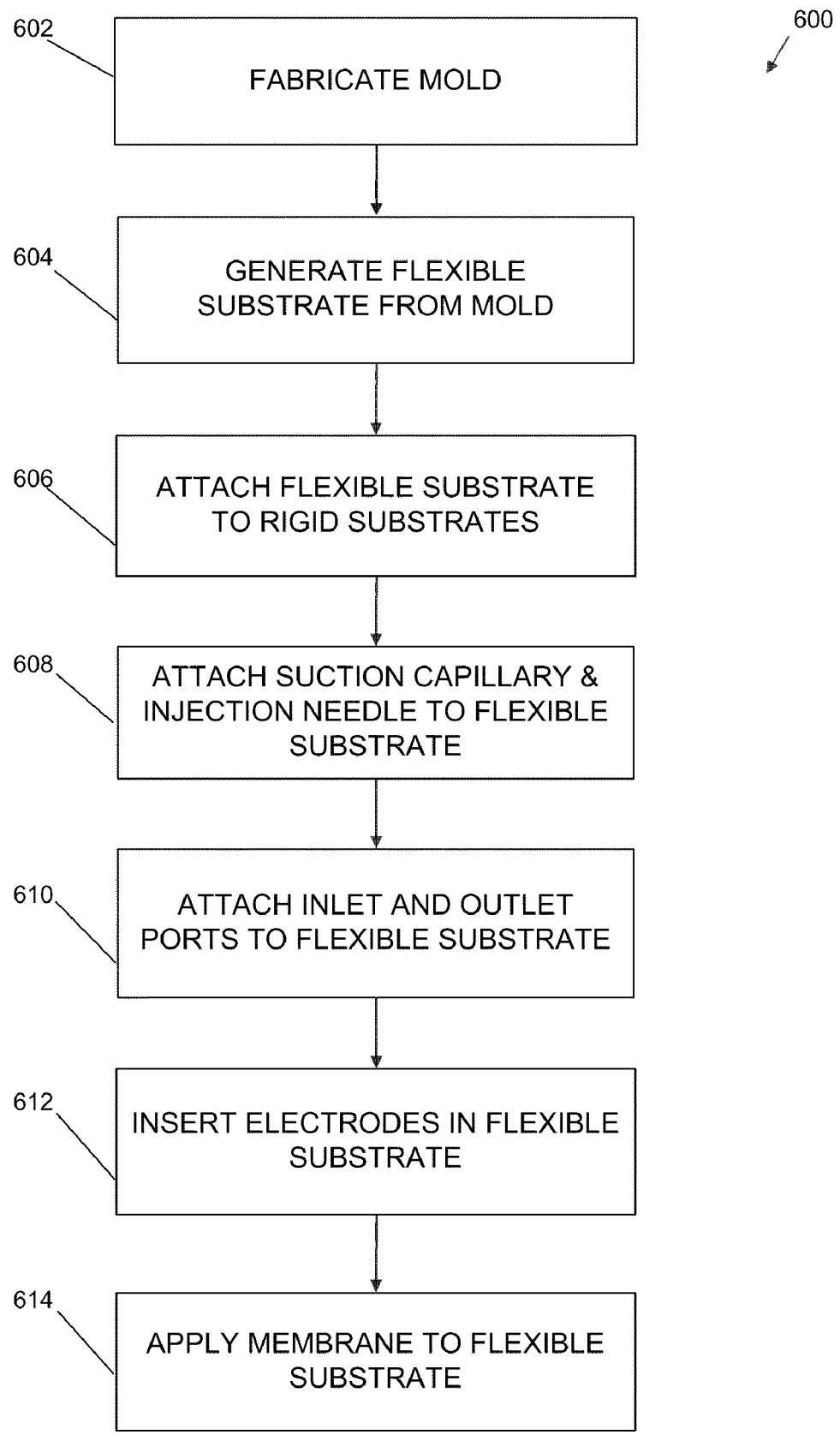
FIG. 13 is a flowchart of a method of manufacturing the microinjection device of FIG. 1 in accordance with an embodiment.

Reference is now made to FIG. 13, in which a method 600 for manufacturing the microinjection device 100 of FIG. 1 in accordance with an embodiment is illustrated. Reference is also made to FIGS. 14A to 14C, in which a microinjection device during different stages of the manufacturing process is illustrated. At step 602, a negative base mold 702 (FIG. 14A) for the flexible substrate 102 is fabricated. In one embodiment, a 3D polymer printer, such as the Dimension™ BST 768, is used to generate the base mold 702. Using such a polymer printer obviates the need for costly cleanroom access and enables true 'rapid prototyping' since the base mold 702 can be generated in a span of minutes rather than hours. The base mold 702 may be made out of acrylonitrile butadiene styrene (ABS) or any other suitable material. Once the base mold 702 fabrication is complete, the method 600 proceeds to step 604.

At step 604, the flexible substrate 102 is created from the base mold 702 (FIG. 14B). This typically involves casting a polymer solution, such as PDMS pre-polymer, into the base mold 702. In some embodiments, a 1:30 volumetric mixture of curing agent to base is used for the PDMS to achieve a certain flexibility for the flexible substrate 102. The thickness of the flexible substrate 102 is typically controlled by pouring a pre-determined volume of the polymer solution in the base mold 702. In some embodiments, the volume is selected to achieve a 0.5 mm thick bottom wall for the target and reagent supply channels 104 and 106. Typically after casting the polymer solution into the base mold 702, the base mold 702, including the polymer solution, is heated and allowed to cure. For example, in one embodiment, the base mold 702 is placed on a heated element, such as a hot plate, and allowed to cure at 65° C. for four hours. After the curing is complete the flexible substrate 102 is peeled from the base mold 702. Once this step is complete, the method 600 proceeds to step 606.

At step 606, the flexible substrate 102 generated in step 604 is attached to the two rigid substrates 136 and 138 (FIG. 14C). In one embodiment, the flexible substrate 102 is bonded to the rigid substrates 136 and 138 using an adhesive agent, such as PDMS pre-polymer. As described above in reference to FIG. 1, the flexible substrate 102 is attached to the rigid substrates 136 and 138 so that (i) there is a gap 140 between the first and second rigid substrates 136 and 138; and (ii) the main section 112 of the target supply channel 104 is situated in the gap 140. In this manner all regions of the flexible substrate 102 are supported by the rigid substrates 136 and 138 except the main section 112 of the target supply channel 104. In some embodiments, the width of the gap 140 is equal to the width of the target supply channel 104. For example, if the target supply channel 104 has a width of 2 mm, the rigid substrates 136 and 138 may be placed 2 mm apart to accommodate the main section 112 of the target supply channel 104.

In some embodiments, a fixture is used to immobilize the rigid substrates 136 and 138 in parallel alignment and with the appropriate spacing or gap 140 to ensure accurate alignment. The flexible substrate 102 may then be carefully placed on the rigid substrates 136 and 138 and aligned using a microscope. After the flexible substrate 102 has been placed on the rigid substrates 136 and 138, the combined structure may be heated to allow the adhesive to cure. For example, in one embodiment, the combined structure is placed onto a heated surface, such as a hotplate, at 65° C. for 10 minutes. The specific temperature and duration of heating are typically based on the materials used for the flexible substrate, the rigid substrate and the adhesive to bond the substrates together. Once the adhesive has cured, the method 600 proceeds to step 608.

At step 608, the suction capillary 132 and the injection needle 134 are attached to the flexible substrate 102 (FIG. 14C). Specifically, the flexible substrate 102 includes suction and needle channels 128 and 130 formed therein which house the suction capillary 132 and the injection needle 134 respectively.

In some embodiments, the injection needle 134 is fabricated using a micropipetter puller, such as a Sutter P97 micropipette puller.

In one embodiment, the injection needle 134 is manually cleaved to obtain a predetermined inner and outer diameter tip. However, manually cleaving the injection needle is typically time consuming. In one embodiment, the predetermined inner and outer diameter tip is 15 µM and 7.7 µm respectively.

Figures 15A, 15B, 15C:
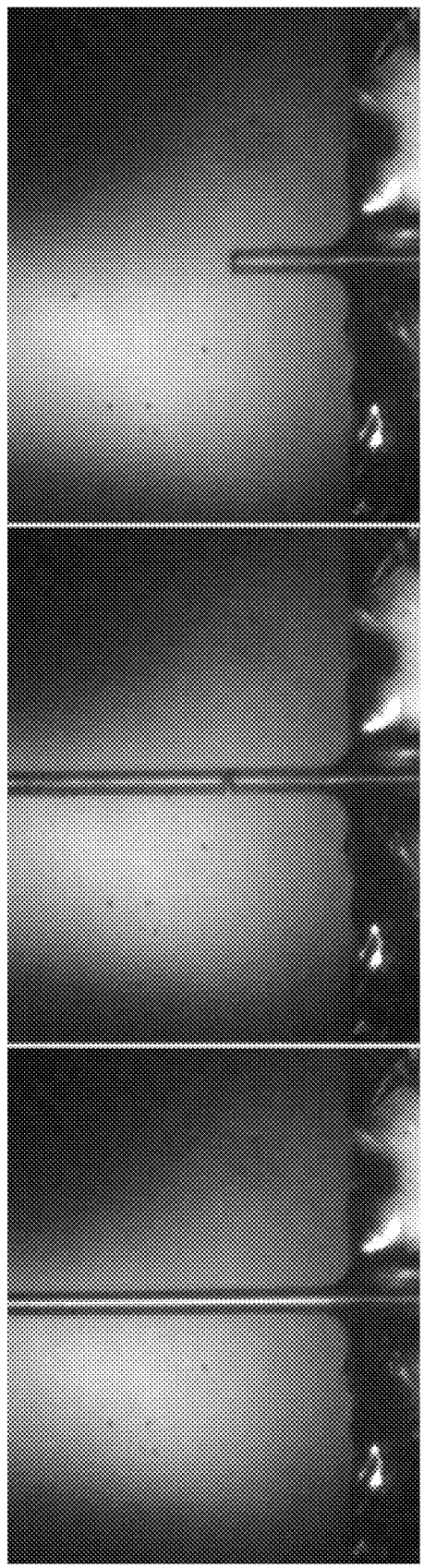
FIGS. 15A to 15C are side views of an injection needle being cleaved using a femtosecond laser in accordance with an embodiment.

In another embodiment, the injection needle 134 is cleaved using a femtosecond laser. For example, the injection needle 134 may be cleaved or cut using a Spectra Physics titanium-doped sapphire chirped-pulse amplifier (CPA) laser system. Such a process typically requires 5 passes and 10 seconds to cut the injection needle 134. A translation speed of 500 µm/s and 0.903 mW power level may be used for this process. Exemplary results of such as process are shown in FIGS. 15A to 15C. Specifically, FIG. 15A shows an uncut injection needle, and FIGS. 15B and 15C show the injection needle after two and five passes later, respectively. Using a femtosecond laser allows the injection needle to be cleaved much more quickly than by a manual cleaving process. Another benefit of this process is that this processing can be done in-situ prior to the sealing of the device.

In yet another embodiment, the injection needle 134 is cleaved using a Focused-Ion-Beam system, such as the LEO/Zeiss 1540SG FIB/SEM CrossBeam. The FIB uses a beam of high-energy gallium ions to mill and ablate an underlying material. Exemplary results using a FIB system are illustrated in FIGS. 16A to 16D. Specifically, FIG. 16A shows an uncut injection needle, FIGS. 16B and 16C show the gradual sharpening of the injection needle, and FIG. 16D shows a front view of the sharpened injection needle. In the exemplary results, the width of the tip of the injection needle was reduced from about 20 μm to about 10 μm.

The sharpening of the injection needle tip through this process may reduce the amount of damage that is caused to the target 202 during an injection. However, if the injection needle is cleaved using a FIB system, the cleaving cannot be performed in-situ due to the limited size of the FIB/SEM loading chamber. Furthermore, to prevent the charging of the needle during the cutting it should be made conductive. This may be achieved by sputter coating the injection needle with gold. The gold would then typically be etched off prior to assembly. This makes the cutting process complex. In addition, cutting the injection needle using a FIB system is a costly and time consuming process which may take several hours.

In one embodiment, the suction capillary 132 and the injection needle 134 are inserted into the suction and needle channels 128 and 130 respectively using a microscope. The end of the suction capillary 132 may be aligned to be flush with the side walls of the target supply channel 104. Conversely, the end of the injection needle 134 may be positioned to extend a predetermined amount into the target supply channel 104. In one embodiment, the injection needle 134 is positioned to extend half way (i.e. 1 mm) into the target supply channel 104. Proper of alignment of the suction capillary 132 and the injection needle 134 may be achieved using digital images and adjusting the position of the injection needle 134 accordingly.

Once a satisfactory alignment has been obtained, the suction capillary 132 and the injection needle 134 are attached to the suction and needle channels 128 and 130 respectively using, for example, an adhesive. In one embodiment, drops of PDMS pre-polymer are attached into the needle and suction channels 128 and 130 then the device is heated to allow the adhesive to cure. For example, the device may be placed on a heated element, such as a hotplate, at 65° C. for 10 minutes. The specific temperature and duration of heating are typically based on the materials used for the flexible substrate, the suction capillary/injection needle, and the adhesive to bond the suction capillary and injection needle to the flexible substrate. Once the adhesive has cured, the method 600 proceeds to step 610.

At step 610, the channel inlet and outlet ports 120, 122, 124 and 126 are attached to the inlet and outlet sections of the target and reagent supply channels 104 and 106. In one embodiment, the channel inlet and outlet ports 120, 122, 124 and 126 are created from long hollow glass capillaries. Suitable glass capillaries include glass capillaries with a 2 mm outer diameter (OD) and a 1.5 mm inner diameter (ID). In one embodiment, the channel inlet and outlet ports 120, 122, 124 and 126 are bonded into holes that are punched into the inlet and outlet sections 108, 110, 116 and 118 of the target and reagent supply channels 104 and 106 and sealed using an suitable adhesive, such as PDMS pre-polymer. Once the channel inlet and outlet ports 120, 122, 124, and 126 are attached to the target and reagent supply channels 104 and 106, the method 600 proceeds to step 612.

At step 612, the electrodes 144 and 146 are inserted into the target and reagent supply channels 104 and 106. As described above in relation to FIG. 1, the electrodes 144 and 146 apply a voltage potential to induce electroosmotic flow through the injection needle 134. In some embodiments, the electrodes 144 and 146 are 30 gauge stainless steel needles. However, in other embodiments, other suitable electrodes may be used.

In some embodiments, the electrodes 144 and 146 are inserted into the target and reagent supply channels 104 and 106 from the side. Once inserted into the appropriate supply channels, the electrodes may be bonded to the flexible substrate 102 using a suitable adhesive, such as PDMS pre-polymer. Once the electrodes 144 and 146 are inserted in the target and reagent supply channels 104 and 106, the method 600 proceeds to step 614.

At step 614, the microinjection device 100 is enclosed using a thin membrane 704, such as a 150 μm PDMS membrane. In one embodiment, a suitable adhesive, such as PDMS pre-polymer, is deposited onto the assembled microinjection device 100 and the membrane 704 is rolled on. The microinjection device 100 including the membrane 604 is then heated until the adhesive cures. For example, the microinjection device 100 may be placed on a heating element, such as a hotplate, at 65° C. for 20 minutes. The specific temperature and duration of heating are typically based on the materials used for the flexible substrate, the membrane and the adhesive to bond the membrane to the flexible substrate.

In some embodiments, the membrane is fabricated by spinning a 1:30 crosslinker:base mixture of PDMS at 400 rpm for 60 seconds onto a silicon wafer. The silicon wafer may be coated with parlene to facilitate the peeling of the membrane.

The inventors have successfully fabricated and tested a microinjection device capable of capturing and electroosmotically injecting Zebrafish embryos (Danio rerio) with methylene blue, rhodamine B and ultrapure water solutions. Reference is now made to FIGS. 17A to 17D, which illustrate the injection of a Zebrafish embryo using the microinjection device 100 of FIG. 1. Specifically, FIG. 17A shows the embryo immobilized by the suction capillary. After immobilization, the embryo is punctured by the injection needle (FIG. 17B). A methylene blue solution is then pumped into the embryo by applying a 25 V potential for 10 seconds to the embedded electrodes (FIG. 17C). Upon completion of the reagent transport, the injection needle is retracted (FIG. 17D) and the embryo is dislodged from the suction capillary by applying a positive pressure. The embryo is then transported in the target channel to the final storage reservoir.

Typically the time required for the injection is dependent on the actuation speed of the injection needle and the reagent volume required. In this exemplary case the total injection time was approximately 15 seconds. Inserting and retracing the injection needle from the embryo took approximately 5 seconds and was achieved using a manually operated linear micropositioner. It is expected that this time can be reduced to 1-2 seconds by using electric or automated actuator. Accordingly, the rate determining step for the injection is the time required for the reagent transport. Typically this varies based on the properties of the embryo, the reagent and the reagent volume that needs to be injected.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto.

The invention claimed is:

1. A microinjection device for injecting a target cell with a reagent, the microinjection device comprising:
   a flexible substrate;

a target supply channel formed in the flexible substrate for receiving the target cell;

a reagent supply channel formed in the flexible substrate for receiving the reagent;

a suction capillary mounted within a suction channel formed in the flexible substrate, the suction capillary providing suction to the target supply channel for immobilizing the target cell within the target supply channel;

an injection needle mounted within a needle channel formed in the flexible substrate, the injection needle being movable between an injected position and an un-injected position by deforming at least a part of the flexible substrate; and a plurality of electrodes embedded in the flexible substrate, the plurality of electrodes creating a voltage potential across the injection needle to move the reagent into the target when the injection needle is in the injected position.

2. The microinjection device of claim 1, wherein the target supply channel, the reagent supply channel, the suction capillary, the injection needle and the plurality of electrodes lie in a single plane of visualization.

3. The microinjection device of claim 1, further comprising first and second rigid substrates, the flexible substrate being mounted to the first and second rigid substrates so that the flexible substrate is deformable by moving the second rigid substrate in at least one direction with respect to the first rigid substrate.

4. The microinjection device of claim 3, further comprising a micropositioner for moving the second rigid substrate in the at least one direction.

5. The microinjection device of claim 4, wherein the micropositioner is at least one of a manual and an automated micropositioner.

6. The microinjection device of claim 3, wherein the second rigid substrate is movable in a single linear direction.

7. The microinjection device of claim 6, wherein the suction channel and the needle channel are situated on an axis perpendicular to the target supply channel, and the second rigid substrate is linearly moveable along the axis.

8. The microinjection device of claim 1, wherein the reagent is moved into the injection needle by electroosmotic flow induced by the voltage potential.

9. The microinjection device of claim 8, wherein the reagent is moved into the injection needle by electoosmotic flow and electrophoretic flow induced by the voltage potential.

10. The microinjection device of claim 1, wherein the location of the injection needle is determined based on electrical current generated by the electrical potential.

11. The microinjection device of claim 1, wherein the location of the injection needle is determined based on electrical current generated by the electrical potential and resistance in a conduction path.

* * * * *